(12) United States Patent
Xu et al.

(10) Patent No.: US 11,624,659 B2
(45) Date of Patent: Apr. 11, 2023

(54) PROBE STRUCTURE AND THERMOMETER

(71) Applicant: Yongjie Gao, Shenzhen (CN)

(72) Inventors: Jing Xu, Shenzhen (CN); Facong Ou, Shenzhen (CN); Qihuan Zhao, Shenzhen (CN)

(73) Assignee: Yongjie Gao, Shenzhen (CN)

( * ) Notice: Subject to any disclaimer, the term of this patent is extended or adjusted under 35 U.S.C. 154(b) by 39 days.

(21) Appl. No.: 17/439,396

(22) PCT Filed: Dec. 2, 2019

(86) PCT No.: PCT/CN2019/122311
§ 371 (c)(1),
(2) Date: Sep. 14, 2021

(87) PCT Pub. No.: WO2020/238117
PCT Pub. Date: Dec. 3, 2020

(65) Prior Publication Data
US 2022/0146323 A1    May 12, 2022

(30) Foreign Application Priority Data
May 25, 2019  (CN) .......................... 201910442448.1

(51) Int. Cl.
*G01J 5/00* (2022.01)
*G01J 5/08* (2022.01)
(Continued)

(52) U.S. Cl.
CPC .............. *G01J 5/0896* (2013.01); *A61B 5/01* (2013.01); *G01K 13/223* (2021.01)

(58) Field of Classification Search
CPC ........ G01J 5/0896; A61B 5/01; G01K 13/223
(Continued)

(56) References Cited

U.S. PATENT DOCUMENTS 6,109,782 A * 8/2000 Fukura ...................... G01J 5/06
374/208
6,886,979 B2 * 5/2005 Conforti .................. G01K 1/08
374/208
(Continued)

FOREIGN PATENT DOCUMENTS

CN    106037680 A    10/2016
CN    106510647 A    3/2017
(Continued)

*Primary Examiner* — Gail Kaplan Verbitsky
(74) *Attorney, Agent, or Firm* — Cheng-Ju Chiang

(57) ABSTRACT

This invention discloses a probe structure and a thermometer, simply-structured but easy to use for users in a dark environment. The technique solution adopted in this invention is a probe structure, including a probe main body, a temperature sensor module and an optical assembly. The probe main body includes a detection end and a configuration end. The detection end is configured for touching or approaching an object. The configuration end is configured for connecting to an external thermometer body. The probe main body has a chamber for storing the temperature sensor module. The optical assembly is positioned at the configuration end. The optical assembly includes at least one lamp, a lamp panel and a light transmitting component. The at-least-one lamp is positioned at the lamp panel and the light transmitting component is disposed at the periphery of the lamp panel. Light emitted by the lamp passes through the light transmitting component.

20 Claims, 7 Drawing Sheets

(51) Int. Cl.
*A61B 5/01* (2006.01)
*G01K 13/20* (2021.01)

(58) Field of Classification Search
USPC ....... 374/121, 120; 600/474, 549; 250/338.1
See application file for complete search history.

(56) References Cited

U.S. PATENT DOCUMENTS

| | | | | |
|---|---|---|---|---|
| 7,001,066 | B1* | 2/2006 | Bellifemine | G01J 5/0815 374/208 |
| 7,390,124 | B2* | 6/2008 | Kienitz | G01J 5/084 374/131 |
| 7,537,381 | B2* | 5/2009 | Hollander | G01J 5/04 374/142 |
| 7,854,550 | B2* | 12/2010 | Chan | G01J 5/0022 374/208 |
| 9,801,730 | B2* | 10/2017 | Howard | A61F 2/4455 |
| 11,172,825 | B1* | 11/2021 | Ayanruoh | A61B 3/12 |
| 2003/0099277 | A1* | 5/2003 | Bellifemine | G01J 5/08 374/121 |
| 2005/0080354 | A1* | 4/2005 | Crossley | A61B 1/2275 600/549 |
| 2005/0085733 | A1 | 4/2005 | Wong | |
| 2017/0322093 | A1 | 11/2017 | Dutterer | |

FOREIGN PATENT DOCUMENTS

| | | | | |
|---|---|---|---|---|
| CN | 208238936 | U | 12/2018 | |
| CN | 110108387 | A | 8/2019 | |
| WO | WO-9801730 | A1 * | 1/1998 | ................ G01J 5/04 |
| WO | 2013/007011 | A1 | 1/2013 | |
| WO | 2016/161297 | A1 | 10/2016 | |

* cited by examiner

PROBE STRUCTURE AND THERMOMETER

CROSS REFERENCE TO RELATED APPLICATIONS

The present application is a 35 U.S.C. § 371 National Phase conversion of International (PCT) Patent Application No. PCT/CN2019/122311, filed on Dec. 2, 2019, which claims benefit of Chinese patent application No. 201910442448.1 filed on May 25, 2019, the disclosure of which is incorporated by reference herein. The PCT International Patent Application was filed and published in Chinese.

FIELD OF THE INVENTION

This invention generally relates to measurement of body temperature of a human. More particularly, this invention relates to a probe structure and a thermometer.

BACKGROUND OF THE INVENTION

Temperature is an important indicator in measuring human health condition. A thermometer is a basic medical tool in family life and clinic medicine. With the development of technologies, infrared technique in temperature measurement of human body has been in wide-spread use. It satisfies human's needs in modern temperature measurement of humans with instant response and high accuracy.

In prior art, thermometers with infrared temperature measurement techniques include ear thermometers and forehead thermometers. Ear thermometer users need to insert the probe at the front end of the thermometer into the ears or the mouth to measure human body temperature; forehead thermometer users need to aim the probe to their forehead to measure human body temperature. In the process of realizing this invention, the inventor found that when using the prior art thermometers, it is difficult to aim the probe accurately to a target spot in a dark environment at night. It is especially challenging to quickly insert an ear thermometer probe into an ear or a mouth in a dark environment.

SUMMARY OF THE INVENTION

The goal of this invention is to provide a probe structure and a thermometer, simply-structured and easy to use for users in a dark environment.

To realize the above-mentioned goal, this invention adopts the following technique solutions.

This invention discloses a probe structure, including a probe main body, a temperature sensor module and an optical assembly. The probe main body includes a detection end and a configuration end. The detection end is configured for touching or approaching an object to be measured. The configuration end is configured for connecting to an external thermometer body. The probe main body has a chamber for storing the temperature sensor module. The optical assembly is positioned at the configuration end. The optical assembly includes at least one lamp, a lamp panel and a light transmitting component. The at least one lamp is positioned at the lamp panel and the light transmitting component is disposed at the periphery of the lamp panel so that light of the lamp is capable of emitting through the light transmitting component.

Preferably, this technique solution further comprises a forehead thermometer cover. The forehead thermometer cover is configured for covering the outer surface of the probe main body and does not cover the light transmitting component when coupled to the probe main body.

Preferably, in this technique solution, the lamp emits at least light of two different colors so as to send different signals by changing the color of light; or the lamp can have a light-on mode or a flash mode to send different signals.

Preferably, in this technique solution, the outer side surface of the light transmitting component in a radial direction protrudes the outer side surface of the probe main body in a radial direction so that the external forehead thermometer cover does cover the light transmitting component when coupled to the probe main body.

Preferably, in this technique solution, since the lamp panel, in an axial direction, has a surface towards the detection end and a surface away from the detection end, the lamp is arranged on the surface away from the detection end; or since the lamp, in an axial direction, has an interior configuration surface and an exterior configuration surface, the lamp is disposed at the exterior configuration surface.

Preferably, in this technique solution, the optical assembly has at least three lamps evenly distributed on the lamp panel; the lamp panel is a printed circuit board.

Preferably, in this technique solution, the configuration end has a connection structure to connect to an external thermometer body. The lamp is coupled with the connection structure. The light transmitting component is sleeved on the periphery of the lamp panel.

Preferably, in this technique solution, the end surface of the connection structure protrudes from the end surface of the configuration end. The lamp panel is coupled with the part of the connection structure protruding from the end surface of the configuration end.

Preferably, in this technique solution, the configuration end further comprises a fixing structure configured for limiting the rotation of the lamp panel.

Preferably, in this technique, the fixing structure includes a cooperation solution of a bulge and a groove. Either of the configuration end or the lamp panel is further provided with the bulge, and the other is provided with the groove; or the fixing structure includes a clamping solution with the lamp panel clamping on the configuration end.

Preferably, in this technique solution, the configuration end further comprises a limiting structure configured for limiting the rotation of the light transmitting component.

Preferably, in this technique solution, the limiting structure in this technical solution includes a cooperation solution of a protrusion and a recess, wherein either the configuration end or the light transmitting component is further provided with the protrusion, and the other is provided with the recess; or the limiting structure includes a clamping scheme, and the light transmitting component is clamped at the configuration end.

Preferably, in this technique solution, the optical assembly further includes a light reflector. The light reflector touches or approaches the light transmitting component so that at least one part of the light through the light transmitting component emits toward a predetermined direction.

Preferably, in this technique solution, the light transmitting component has an inclined surface at the juncture of the outer side surface in a radial direction and the bottom surface. The light reflector sleeves on the inclined surface of the light transmitting component. The light reflector at least has a reflective layer on the part touching the inclined surface.

Preferably, in this technique, the inclined surface is away from the detection end. The inclined surface has an angle of 45 degrees.

Preferably, in this technique, the predetermined direction is the direction toward the detection end.

Preferably, in this technique, the outer side surface of the light reflector in a radial direction and the outer side surface of the light transmitting component in a radial direction are mainly on the same plane. The bottom surface of the light reflector and the bottom surface the light transmitting component are mainly at the same plane.

This invention further discloses a thermometer, including a thermometer body and a probe. The probe is the probe structure according to any of the descriptions in the above technique solution. When the configuration end connects to the thermometer body, the light transmitting component is positioned between the probe and the thermometer body.

Preferably, in this technique, the thermometer body is further provided with a display. The display and the lamp are capable of emitting at least light of two different colors. The color of light from the display and that from the lamp remain the same; or the display and the lamp remain on or flash simultaneously.

Compared with prior art, the beneficial effects are: since the probe structure and the thermometer both include a lamp, a lamp panel and a light transmitting component, when the thermometer with the probe structure is in use, light from the lamp provides illumination for the user to easily aim the target or know the position of the probe structure so that the thermometer is easy and convenient to use in a dark environment. And since the optical assembly is arranged at the configuration end, when the probe is inserted into an ear or a mouth, light from the optical assembly will not be blocked. Because the lamp is arranged and integrated on the lamp panel and the light transmitting component is arranged on the periphery of the lamp panel, the technique solution provided in this invention is easy to manufacture and assemble due to a few structure components, and simple structure assembly processes.

Other advantages of this invention will be further illustrated in preferred embodiments.

BRIEF DESCRIPTION OF THE DRAWINGS

To better illustrate the technique solution in the preferred embodiments of this invention, below is a brief introduction of drawings used in embodiment description. Obviously, the drawings in the following description are only some embodiments of the present invention. On account of these drawing, those of ordinary skill in the art can also obtain, without creative work, other drawings.

DETAILED DESCRIPTION OF THE INVENTION

To better illustrate the technical problem, the technical solutions and advantages of the present disclosure, embodiments will now be described in detail below with references to the drawings. It is to be understood that the preferred embodiments described in this part are only to be considered as illustrating the present disclosure instead of limiting the scope of the present disclosure.

The First Embodiment

Figure 1:
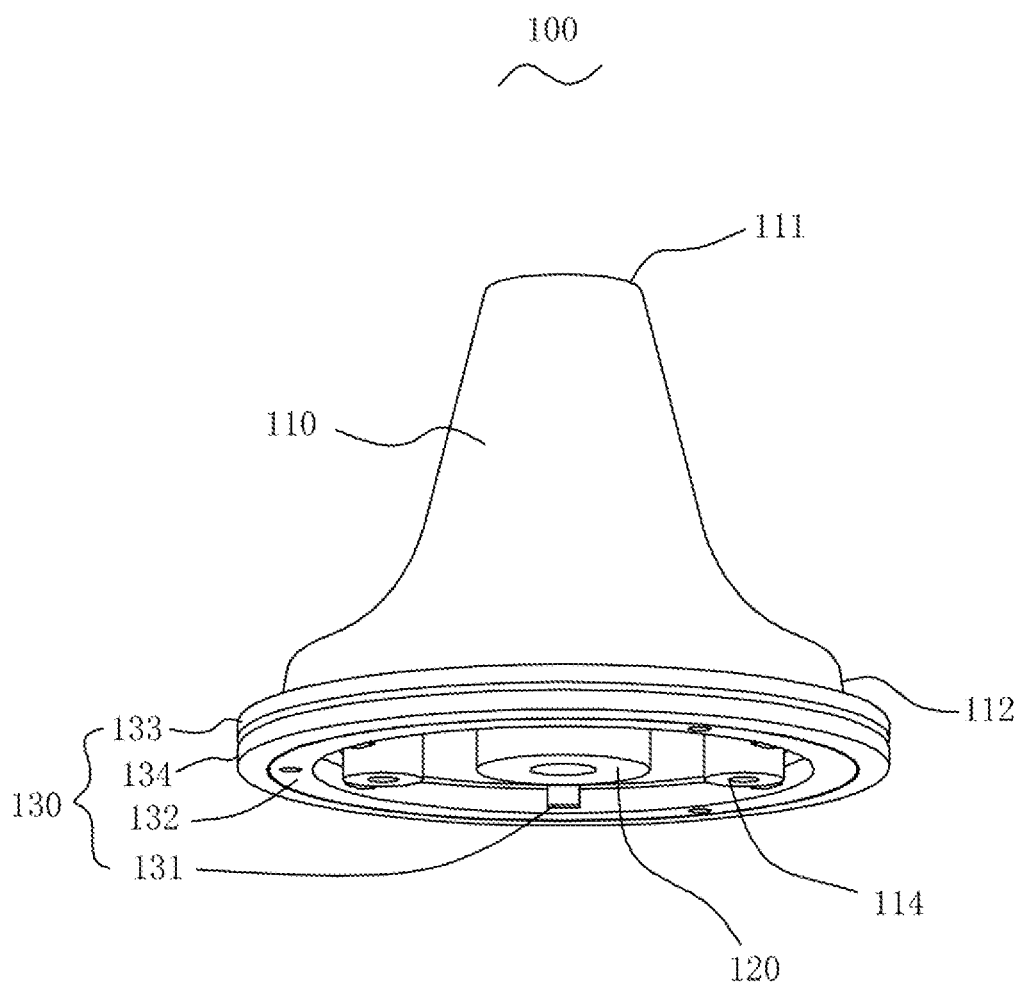
FIG. 1 is a perspective view of the probe structure in the first embodiment.
Figure 2:
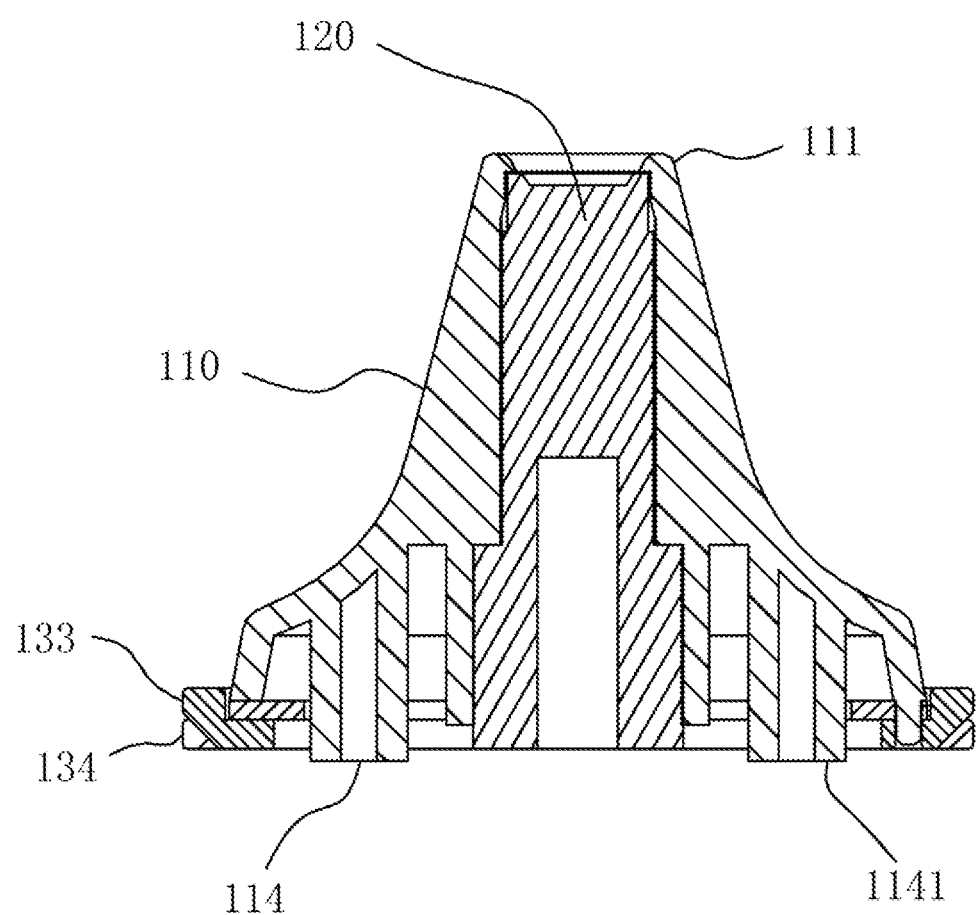
FIG. 2 is a structural section view of FIG. 1.
Figure 3:
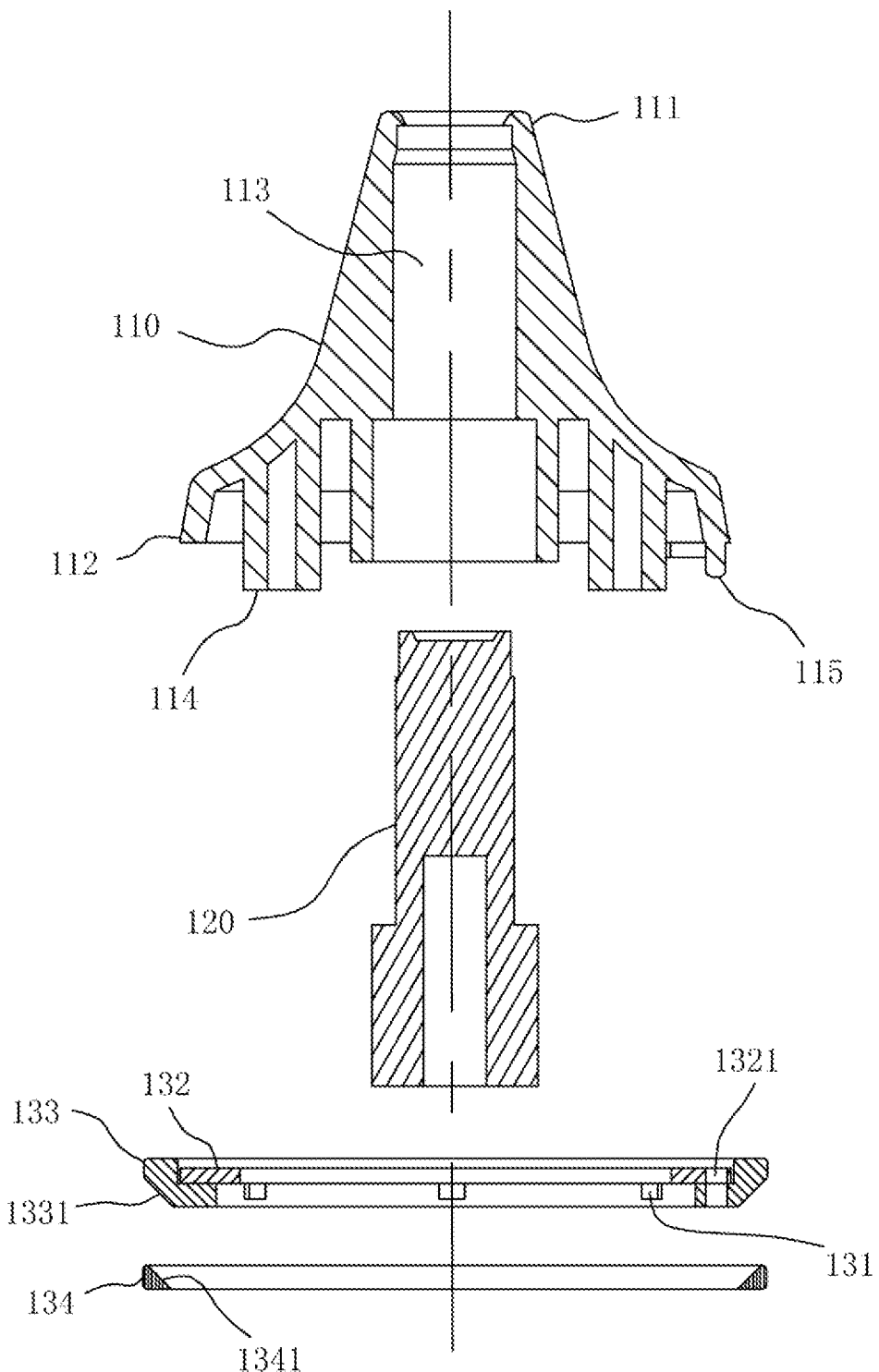
FIG. 3 is a structural exploded schematic view of FIG. 2.

As shown in FIG. 1, the preferred embodiment discloses a probe structure 100, including a probe main body 110, a temperature module 120 and an optical assembly 130. The probe main body 100 includes a detection end 111 and a configuration end 112. The detection end 111 is configured for touching or approaching an object to be measured. The configuration end 112 has a connection structure 114. The configuration end 112 is configured for connecting to an external thermometer body 200 (referring to FIG. 5) through the connection structure 114. As shown in FIG. 2 and FIG. 3, the probe main body 110 has a chamber 113 for storing the temperature sensor module 120. The chamber 113 has an open tube structure. The optical assembly 130 is positioned at the configuration end 112. The optical assembly 130 includes a plurality of lamp 131, a lamp panel 132, a light transmitting component 133 and a light reflector 134. The lamps 131 are arranged on the lamp panel 132. The light transmitting component 133 is sleeved around the lamp panel 132 and light emitted from the lamps 131 passes through the light transmitting component 133. The light reflector 134 touches or approaches the light transmitting component 133 so that at least some light transmitted through light transmitting component 133 emits toward a predetermined direction. In this embodiment, the predetermined direction is the direction toward the detection end 111 so that the light is capable of serving as an illumination purpose. The connection structure 114 is a threaded column structure with internal thread. In other embodiments, the connection structure can also be a clamp structure.

Figure 4:
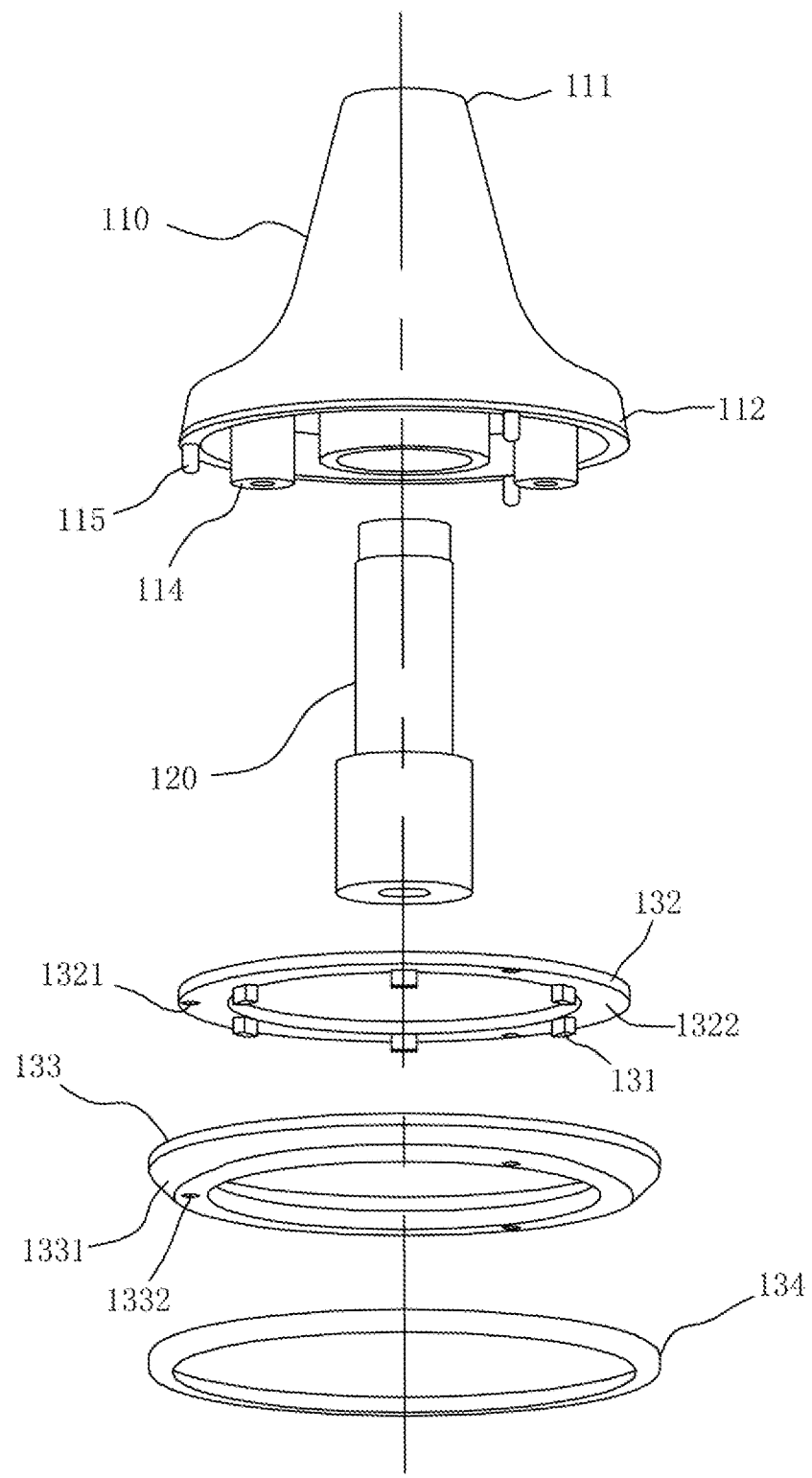
FIG. 4 is a structural exploded schematic view of FIG. 1.

To make the light towards the detection end 111 relatively even, the number of lamps 131 on the optical assembly 130 is preferably three or above three and the lamps 131 are preferably evenly distributed on the lamp panel 132. In this embodiment, as shown in FIG. 4, the number of the lamps 131 is six. The light panel 132 is a printed circuit board. A power input end is provided on the light panel 132. The lamps 131 are electrically connected to the power input end of the lamp panel 132 through circuits. The lamp panel 132, in an axial direction, has a surface (not shown) toward the detection end 111 and a surface 1322 away from the detection end 111. The six lamps 131 are configured on the surface 1322 away from the detection end 111. In other embodiments, when the lamp panel 132, in a radial direction, has an interior configuration surface and an exterior surface, the lamps 131 are preferably configured to be on the exterior surface.

In this embodiment, the lamps 131 are LED lamps of three primary colors. The LED lamps are capable of emitting at least light of at least two different colors so as to send different signals by changing the color of light. For example, when temperature measured by the temperature sensor module 120 is above the predetermined temperature, the lamps 131 emit different colors to remind users. In other embodiments, when the lamps 131 have a light-on mode or a flash mode, if temperature measured by the temperature sensor module 120 is above the predetermined temperature, the lamps 131 remind users by a flash mode.

As shown in FIG. 2, the end surface 1141 of the connection structure 114 protrudes from the end surface of the configuration end 112. The lamp panel 132 is sleeved on the part of the connection structure 114 protruding from the end surface of the configuration end 112. The light transmitting component 133 sleeves on the outside of the lamp panel 132. The outer side surface of the light transmitting component 133 in a radial direction protrudes from the outer side surface of the probe main body 110 in a radial direction so that when an external forehead thermometer cover 300 is on the probe main body 110, the external forehead thermometer cover 300 does not cover the light transmitting component 133 (referring to FIG. 6) or influence light strength.

As shown in FIG. 2 and FIG. 3, configuration end 112 further comprises a fixing structure configured for limiting rotation of the lamp panel 132. The fixing structure is a coordination solution of a bulge 115 and a groove 1321. The configuration end 112 has three bulges 115, and correspondingly the lamp panel 132 has three matching grooves 1321. Besides, the light transmitting component 133 has three grooves 1332 matching the bulges 115. The bulges 115 and the grooves 1332 constitute a limiting structure to limit the rotation of the light transmitting component 133. When the lamp panel 132 and the light transmitting component 133 are assembled, the bulges 115 pass through the groove 1321 and partially go into the grooves 1332 to limit the rotation of the lamp panel 132 and the light transmitting component 133. In other embodiments, the fixing structure and the limiting structure can also be a clamping solution. In the clamping solution, the bulges 115 are changed into a buckle structure and the lamp panel 132 and the light transmitting 133 are clamped on the configuration end 112 through buckles.

As shown in FIG. 2 and FIG. 3, the light transmitting component 133 has an inclined surface 1331 at the juncture of its outer side surface in a radial direction and its bottom surface. The light reflector 134 sleeves on the inclined surface 1331 of the light transmitting component 133. The light reflector 134 at least has a reflective layer on the part touching the inclined surface 1331. In this embodiment, the inclined surface 1331 normally has an angle of 45 degrees. The inclined surface 1331 is positioned away from the detection end 111.

As shown in FIG. 1 and FIG. 2, the outer side surface of the light reflector 134 in a radial direction and the outer side surface of the light transmitting component 133 in a radial direction are mainly on the same plane. The bottom surface of the light reflector 134 and the bottom surface of the light transmitting component 133 are mainly on the same plane. Thus, the outer surface of the light reflector 134 and the surfaces of the light transmitting component 133 it connects to are on the same plane and constitute an integrated smooth structure.

The probe structure 100 includes the lamps 131, the lamp panel 132 and the light transmitting component 133. The lamps 131 are provided on the lamp panel 132. The light transmitting component 133 sleeves on the lamp panel 132 so that light from the lamps 131 is capable of emitting through the light transmitting component 133. Thus, when a thermometer with a probe structure 100 is in use, light from the lamps 131 provide illumination so that users can easily aim at the position being measured and know the position of the probe structure 100, and thermometers can be conveniently used in a dark environment. Because the optical assembly 130 is arranged on the configuration end 112, when the probe structure 100 is used in an ear thermometer and inserted into an ear or a mouth, light from the optical assembly 130 tends not to be blocked; when the probe structure is used in a forehead thermometer, light tends not to be blocked by women's long hair. Because the lamps 131 are integrated on the lamp panel 132 and the light transmitting component 133 sleeves on the lamp panel 132, light from lamp 131 is capable of emitting through the light transmitting component 133. Thus, the solution provided in this embodiment is easy to manufacture and assemble due to a few structural components and simple assembly processes.

The Second Embodiment

Figure 5:
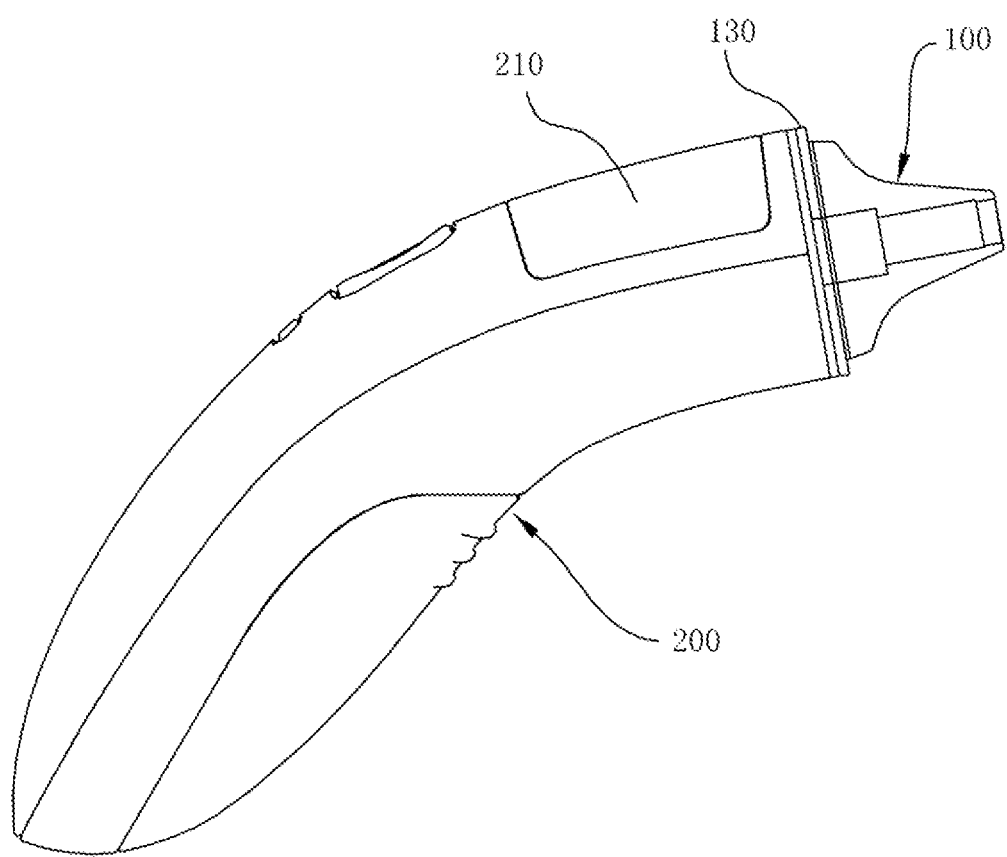
FIG. 5 is a structural elevational view of the thermometer as an ear thermometer.
Figure 6:
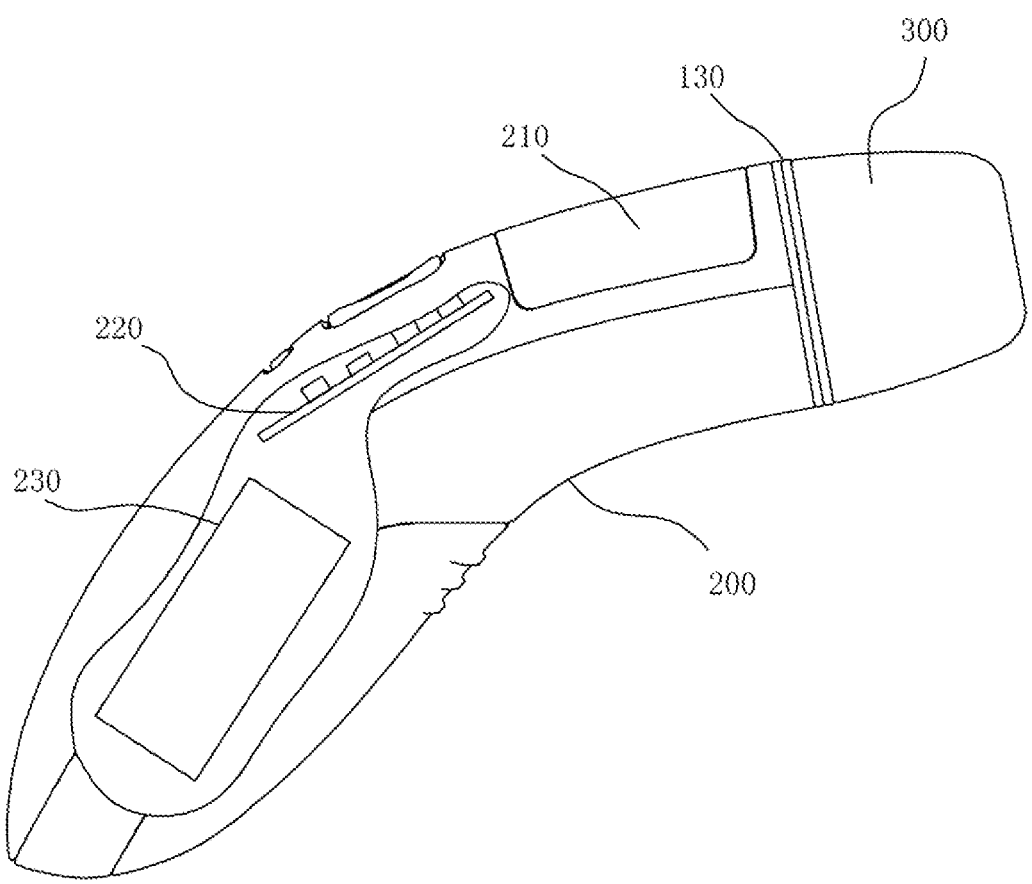
FIG. 6 is a structural elevational view of the thermometer as a forehead thermometer.
Figure 7:
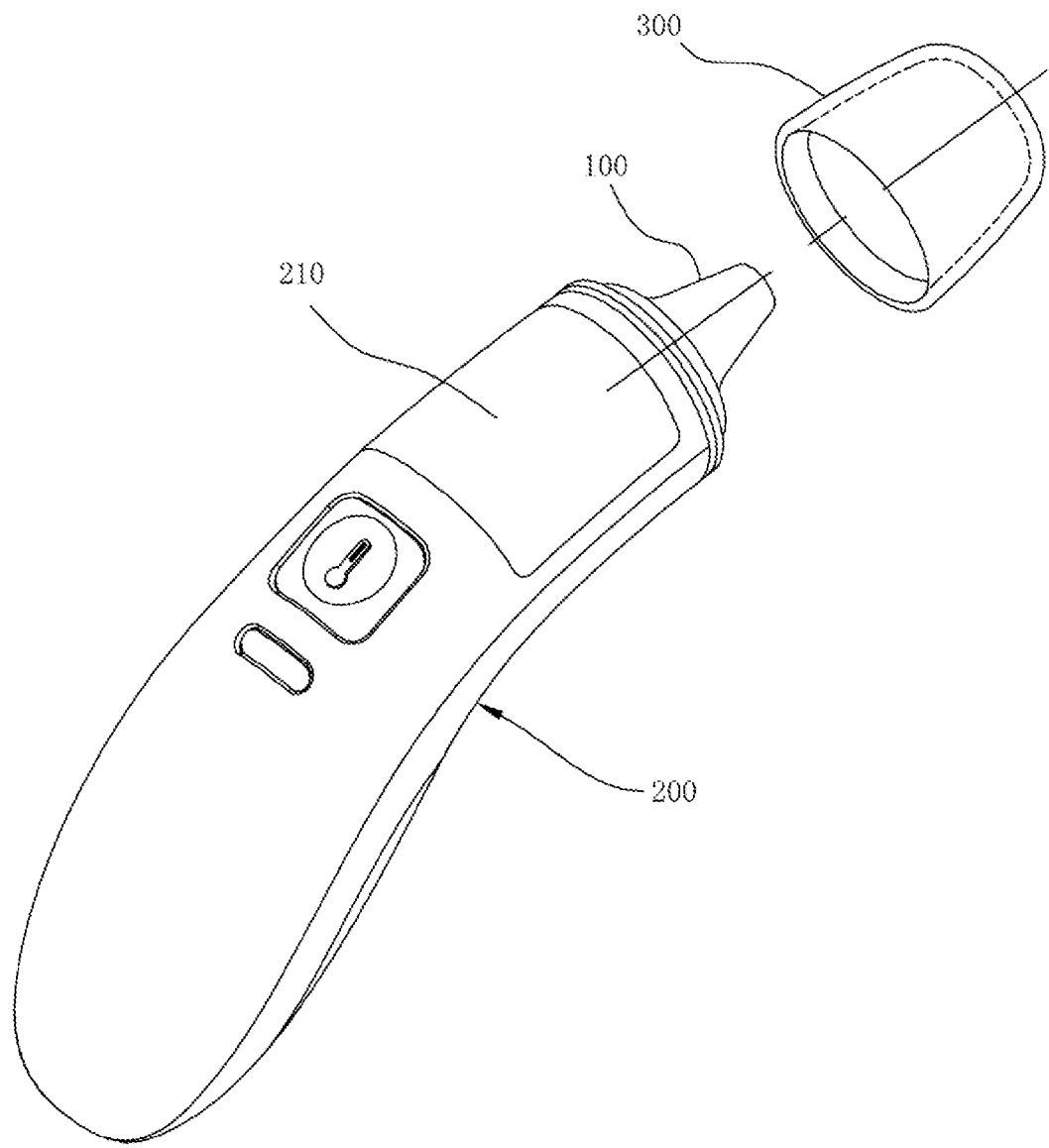
FIG. 7 is a status schematic view of a forehead thermometer formed by an ear thermometer and a forehead thermometer cover.

As shown in FIG. 5, FIG. 6 and FIG. 7, the present embodiment discloses a thermometer, including a thermometer body 200, a probe structure 100 and a forehead thermometer cover 300. The probe structure 100 is the probe structure 100 in the first embodiment. To shorten the length of the writing, the specific structure of the probe structure 100 will not be described more than it is needed.

As shown in FIG. 6 and FIG. 7, the thermometer body 200 includes a display 210, a control panel 220 and a power supply 230. The configuration end 112 is connected to a thermometer body 200 through a connection structure 114 with threaded connection and the lamp panel 132 and the temperature sensor module 120 are connected to the control panel 220 and the power supply 230. The optical assembly 130 is positioned between the probe structure 100 and the thermometer body 300. The forehead thermometer cover 300 is configured for covering the probe main body 110. When covered on the probe structure 100, the forehead thermometer cover 300 does not cover the light transmitting component 133.

In this embodiment, the display 310 has backlight of at least two colors. Colors of light from the display screen 210 and from the lamps 131 remain the same. Specifically, when temperature measured by the temperature sensor module 120 is above the predetermined temperature, the display 210 and the lamps 131 emit red light to remind users. In other embodiments, when the display 210 and the lamps 131 have a light-on mode or a flash mode, the display 210 and the lamps 131 remain on simultaneously or flash simultaneously to send two different messages.

It will be understood that the embodiments of the present invention are only to be considered as illustrating the present disclosure instead of limiting the scope of the present disclosure. It will be apparent to those skilled in the art that modifications and variations can be made without departing from the scope and spirit disclosed by the present disclosure, and such modifications and variations all fall in the protection extent of the present disclosure.

What is claimed is:

1. A probe structure comprising:
a probe main body, a temperature sensor module, and an optical assembly, the probe main body including a detection end and a configuration end, the detection end being configured for touching or approaching an object to be measured, and the configuration end being configured for connecting to an external thermometer body, the probe main body having a chamber for storing the temperature sensor module;
wherein the optical assembly is positioned at the configuration end, the optical assembly includes at least one lamp, a lamp panel, a light transmitting component and a light reflector, the at least one lamp is positioned at the lamp panel, and the light transmitting component is disposed at the periphery of the lamp panel so that light emitted by the at least one lamp can pass through the light transmitting component, the light reflector touches or approaches the light transmitting component so that at least one part of the light through the light transmitting component emits toward a predetermined direction; since the lamp panel, in an axial direction, has a surface towards the detection end and a surface away from the detection end, the lamp is arranged on the surface away from the detection end; or since the lamp panel, in a radial direction, has an interior configuration surface and an exterior configuration surface, the lamp is disposed at the exterior configuration surface.

2. The probe structure of claim 1, further comprising a forehead thermometer cover configured for covering an outer surface of the probe main body and not covering the light transmitting component after the forehead thermometer cover is coupled with the probe main body.

3. The probe structure of claim 1, wherein the at least one lamp emits light of at least two different colors so as to send different signals by changing the color of light; or the lamp uses a light-on mode or a flash mode to send different signals.

4. The probe structure of claim 1, wherein the outer side surface of the light transmitting component in a radial direction protrudes the outer side surface of the probe main body in a radial direction so that the external forehead thermometer cover does not cover the light transmitting component when coupled to the probe main body.

5. The probe structure of claim 1, wherein the optical assembly includes at least three lamps evenly-distributed on the lamp panel; the lamp panel is a printed circuit board.

6. The probe structure of claim 1, wherein the configuration end has a connection structure for connecting to an external thermometer body, the lamp panel sleeves on the connection structure and the light transmitting component sleeves on the periphery of the lamp panel.

7. The probe structure of claim 6, wherein the end surface of the connection structure protrudes from the end surface of the configuration end, the lamp panel is coupled with the part of the connection structure protruding from the end surface of the configuration end.

8. The probe structure of claim 1, wherein the configuration end further comprises a fixing structure configured for limiting the rotation of the lamp panel.

9. The probe structure of claim 7, wherein the fixing structure includes a cooperation solution of a bulge and a groove, either the configuration end or the lamp panel is further provided with the bulge, and the other is provided with the groove; or the fixing structure includes a clamping solution with the lamp panel clamping on the configuration end.

10. The probe structure of claim 1, wherein the configuration end further comprises a limiting structure configured for limiting the rotation of the light transmitting component.

11. The probe structure of claim 10, wherein the limiting structure includes a cooperation solution of a protrusion and a recess, wherein either the configuration end or one of the light transmitting components is further provided with the protrusion, and the other is provided with the recess; or the limiting structure includes a clamping scheme, and the light transmitting component is clamped at the configuration end.

12. The probe structure of claim 1, wherein the light transmitting component has an inclined surface at the juncture of the outer side surface in a radial direction and the bottom surface, the light reflector sleeves on the inclined surface of the light transmitting component, the light reflector at least has a reflective layer on the part touching the inclined surface.

13. The probe structure of claim 12, wherein the inclined surface is away from the detection end, the inclined surface has an angle of 45 degrees.

14. The probe structure of claim 1, wherein the predetermined direction is the direction toward the detection end.

15. The probe structure of claim 1, wherein the outer side surface of the light reflector in a radial direction and the outer side surface of the light transmitting component in a radial direction are mainly on the same plane, the bottom surface of the light reflector and the bottom surface of the light transmitting component are mainly on the same plane.

16. A thermometer, comprising a thermometer body and a probe, wherein the probe comprises a probe main body, a temperature sensor module and an optical assembly, the probe main body includes a detection end and a configuration end, the detection end is configured for touching or approaching an object to be measured, and the configuration end is configured for connecting to an external thermometer body, the probe main body has a chamber for storing the temperature sensor module, the optical assembly is positioned at the configuration end, the optical assembly includes at least one lamp, a lamp panel a light transmitting component and a light reflector, the at least one lamp is positioned at the lamp panel, and the light transmitting component is disposed at the periphery of the lamp panel so that light emitted by the at least one lamp can pass through the light transmitting component, the light reflector touches or approaches the light transmitting component so that at least one part of the light through the light transmitting component emits toward a predetermined direction; since the lamp panel, in an axial direction, has a surface towards the detection end and a surface away from the detection end, the lamp is arranged on the surface away from the detection end; or since the lamp panel, in a radial direction, has an interior configuration surface and an exterior configuration surface, the lamp is disposed at the exterior configuration surface, when the configuration end connects to the thermometer body, the light transmitting component is positioned between the probe and the thermometer body.

17. The thermometer of claim 16, wherein the thermometer body is further provided with a display, the display and the lamp are capable of emitting light of at least two different colors, the color of light from the display and that from the lamp remain the same; or the display and the lamp remain on or flash simultaneously.

18. The thermometer of claim 16, wherein the light transmitting component has an inclined surface at the juncture of the outer side surface in a radial direction and the bottom surface, the light reflector sleeves on the inclined surface of the light transmitting component, the light reflector at least has a reflective layer on the part touching the inclined surface.

19. The thermometer of claim 16, further comprising a forehead thermometer cover configured for covering an outer surface of the probe main body and not covering the light transmitting component after the forehead thermometer cover is coupled with the probe main body.

20. The thermometer of claim 16, wherein the outer side surface of the light reflector in a radial direction and the outer side surface of the light transmitting component in a radial direction are mainly on the same plane, the bottom surface of the light reflector and the bottom surface of the light transmitting component are mainly on the same plane.

* * * * *